United States Patent
McJames, II et al.

[11] Patent Number: 5,935,138
[45] Date of Patent: Aug. 10, 1999

[54] SPIRAL NEEDLE FOR ENDOSCOPIC SURGERY

[75] Inventors: William C. McJames, II, Belle Mead; Donald G. Miller, Three Bridges; Thomas Nering, Milford; Robert Nering, Sergeantsville; Joseph Rollero, Whitehouse Station; Lester E. Schaible, Somerville, all of N.J.

[73] Assignee: Ethicon, Inc., Somerville, N.J.

[21] Appl. No.: 08/937,655

[22] Filed: Sep. 24, 1997

[51] Int. Cl.$^6$ ............................................. A61B 17/10
[52] U.S. Cl. ........................ 606/139; 606/167; 606/228
[58] Field of Search .................................. 606/222–228, 606/167, 142–148, 139

[56] References Cited

U.S. PATENT DOCUMENTS

| | | | |
|---|---|---|---|
| 1,377,359 | 5/1921 | Littlejohn . | |
| 4,204,541 | 5/1980 | Kapitanov | 128/334 R |
| 4,524,771 | 6/1985 | McGregor et al. | 128/339 |
| 4,905,695 | 3/1990 | Bendel et al. | 606/222 |
| 4,959,068 | 9/1990 | Bendel et al. | 606/222 |
| 5,041,127 | 8/1991 | Troutman | 606/223 |
| 5,053,047 | 10/1991 | Yoon | 606/223 |
| 5,356,424 | 10/1994 | Buzerak et al. | 606/223 |
| 5,433,728 | 7/1995 | Kim | 606/223 |
| 5,626,043 | 5/1997 | Bogart et al. | 72/133 |

FOREIGN PATENT DOCUMENTS

| | | | |
|---|---|---|---|
| 0923530 | 8/1980 | U.S.S.R. | 606/148 |
| 923530 | 2/1982 | U.S.S.R. | 606/148 |
| WO 97/16121 | 5/1997 | WIPO . | |

Primary Examiner—Michael Buiz
Assistant Examiner—Lien Nao
Attorney, Agent, or Firm—James Riesenfeld

[57] ABSTRACT

A needle for endoscopic surgery is curved into an arc of more than 180° and twisted, so that it forms a part of a spiral, with a lateral offset between the needle point and barrel. The needle is sized to fit through a 10 mm trocar and is also blackened, to improve its visibility in a bloody field. The needle curvature is preferably not constant over its entire length, so that different sections have different radii of curvature. The needle is particularly well adapted for performing laporascopically a procedure (Burch Colposuspension) that is used to treat female stress incontinence.

11 Claims, 2 Drawing Sheets

SPIRAL NEEDLE FOR ENDOSCOPIC SURGERY

BACKGROUND OF THE INVENTION

1. Field of the Invention

This invention relates to a needle for endoscopic surgery, more particularly, a horseshoe-shaped needle that is twisted out of a single plane.

2. Description of the Related Art

Surgical needles come in a variety of shapes, from straight to curved. Among curved needles, the needle may be "planar", with the entire needle in a single plane, or "aplanar", in which the point and barrel of the needle may be said to be offset from one another. Aplanar needles have been known for many years.

U.S. Pat. No. 1,377,359, issued May 10, 1921, to D. Littlejohn discloses a surgical needle with semicircular bends at each end, the two semicircular regions being in planes that are at right angles to each other. Thus, when the needle is laid upon a flat surface, it always presents an upstanding grasping surface.

U.S. Pat. No. 5,041,127, issued Aug. 20, 1991, to R. Troutman discloses a curved surgical needle that may be planar or aplanar, with the pointed end offset from the principal longitudinal axis. When using the aplanar needle, the offset of the tip of the needle from the body of the needle enables the surgeon to view the tip continuously, without moving her head.

Helical suturing devices are disclosed in U.S. Pat. No. 4,204,541, issued May 27, 1980, to Kapitanov; U.S. Pat. No. 5,053,047, issued Oct. 1, 1991, to Yoon; and U.S. Pat. No. 5,356,424, issued Oct. 18, 1994, to J. Buzerak et al. Kapitanov discloses an instrument for suturing soft tissue. It has a hollow body, housing a hollow helical needle that contains a suture. The needle and suture are introduced into the tissue, and the suture is retained in the tissue as the needle is extracted. Yoon discloses a suture device for endoscopic surgery. The device is a generally helical bioabsorbable material that is sharp at one end, for penetrating tissue, and has filamentary protrusions along its length, which permit forward motion of the material but limit rearward motion. Buzerak et al. disclose a laparoscopic suturing device that includes a helically-wound needle, having a sharp point at the front end and a driver connected to the rear. (See also PCT Application WO97/16121.)

U.S. Pat. No. 4,524,771, issued Jun. 25, 1985, to W. McGregor et al. discloses a surgical needle that comprises a plurality of curves along its length.

U.S. Pat. No. 5,626,043, issued May 6, 1997, to M. Bogart et al. discloses an apparatus for forming curved, rectangular bodied surgical needles. (See also U.S. Pat. No. 5,287,721, issued Feb. 22, 1994, to W. Samsel et al.)

U.S. Pat. No. 4,905,695, issued Mar. 6, 1990, to L. Bendel et al. discloses a blackened surgical needle that is more readily observed by surgeons during surgical procedures than are conventional shiny needles. (See also U.S. Pat. No. 4,959,068, issued Sep. 25, 1990, to L. Bendel et al.)

The disclosures of all the above-mentioned patents are incorporated herein by reference.

SUMMARY OF THE INVENTION

In accordance with the present invention, a needle for endoscopic surgery comprises an elongated solid steel body formed into a generally arcuate shape, with a pointed distal end and a proximal end, in which:

(a) the needle is blackened (b) the needle is dimensioned to fit through a 10 mm diameter trocar; and (c) the body of the needle is not in a single plane, whereby there is a lateral offset of the distal end from the proximal end.

The needle is particularly well-suited for performing procedures like the Burch procedure (used to treat female stress incontinence)laporascopically, since the needle's geometry makes it effective in a tight, confined area and allows excellent visibility while suturing through the ilio pectineal or "Cooper's" ligament. The needle can also be applied to a running suture technique, where the curved part of the needle allows the surgeon to start the needle through the tissue and, with the appropriate turnout, continue stitching. The needle will set itself up for the next stitch automatically.

DETAILED DESCRIPTION OF THE INVENTION

Typical surgical needles are curved or shaped in a generally semicircular fashion. They were originally designed for open procedures rather than the newer endoscopic procedures. As a result, these general surgical needles are not capable of suturing in a confined space through a trocar. Furthermore, a shiny silver needle can easily become lost in a bloody field during endoscopic procedures. A highly visible surgical needle is needed, which provides consistent approximation without deformation in endoscopic surgery.

The present invention relates to a curved surgical needle for use in laparoscopic surgery, such as the Burch procedure for bladder neck suspension. The taperpoint, preferably having a 12:1 taper ratio, provides the needle with a smooth penetration through extremely tough tissue, such as the Cooper's ligament. The needle is blackened, so as to be visible against the background of the bright white ligament. In performing this procedure, the surgeon grasps the needle approximately ⅔ of the way from the front point of the needle with a conventional endoscopic needle holder and passses the needle through the Cooper's ligament by piercing the ligament with the point and rotating the needleholder. The tight curvature of the needle passes through the ligament and quickly returns out of the ligament. The spiral needle preferably has a curvature greater than 180 degrees and preferably has sections of different radius, preferably approximately 5 mm and 7 mm near the center of the needle. For other applications, the radius of the needle can be greater or smaller, depending on the desired bite in the tissue. Smaller radii on the needle provide the surgeon with a tighter bite in the tissue. As a result, the helical geometry can be uniform, kinked (i.e., sharply bent at a point on the needle), or non-uniform, depending on the radii.

When the surgeon rotates the needle holder, the needle moves forward down the tissue and sets itself up for the next pass. The helical offset of the needle is preferably about 4 mm.; however, the needle can also be effective if the offset is greater or less than that. The controlled approximation across the wound is largely determined by the offset.

Conventional endoscopic suturing requires two hands for needle manipulation. With one hand, the surgeon disarms the needle as it is still in the tissue and then rearms the needle near the point. The surgeon then rotates the needleholder and completes the pass through the tissue. The present needle allows the surgeon to suture with one hand. The helical geometry allows the surgeon to regrasp the needle in the proper orientation for the next pass through the tissue, so that control of the needle is maintained and regrasping is greatly simplified.

Figure 1:
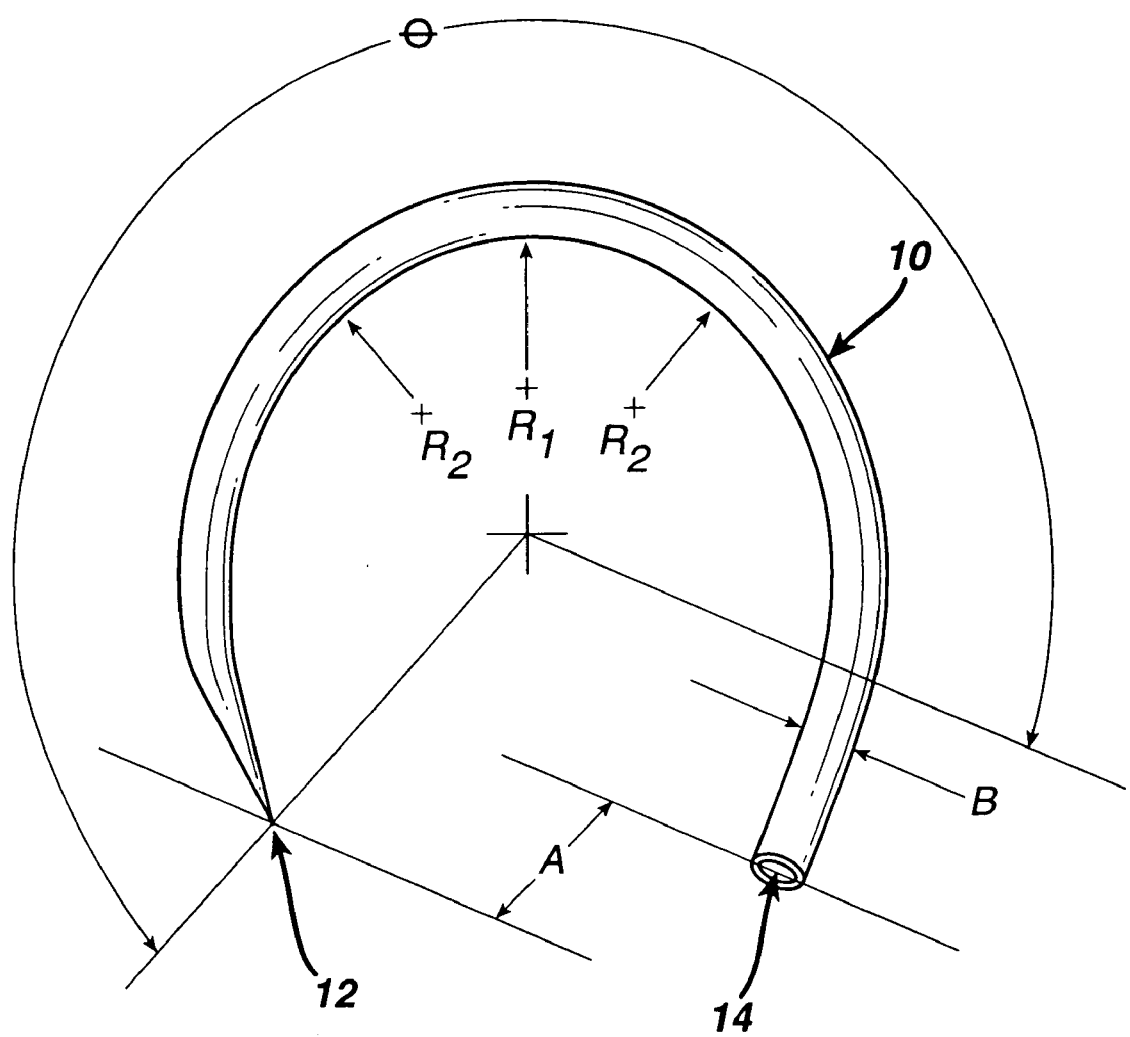
FIG. 1 is a plan view of a needle of the present invention.

FIG. 1 depicts the surgical needle 10 of the present invention. The arc (curvature) of the needle θ is greater than 180°, preferably greater than 225°. Preferably, the curvature radius is not constant over the entire arc. As shown, the central section radius is $R_1$ and the radius of the sections on either side of the central section is $R_2$. The needle is twisted out of a planar arc to form an aplanar, or spiral, shape. Thus, the needle end 12 is offset from the barrel end 14 by a lateral offset A. The offset is preferably about 2 mm to 5 mm, more preferably about 4 mm. The needle diameter B is preferably about 0.2 mm to 2 mm, more preferably about 1 mm. A is preferably about four times B. As shown in FIG. 1, the section of the needle nearest barrel end 14 has a very large radius of curvature, so that it is substantially linear.

The process for producing the spiral needle of this invention is as follows:

The spiral needle is initially straightened to remove the coil shape. Spools of wire, as drawn from the wire mill, are mounted on an adjustably pivoting mount. Surgical grade stainless steel wire is contained on a spool. The height and position of the wire is adjusted using both vertical and horizontal positioning, to align the incoming wire with the centerline of the machine, minimizing undesirable stresses to the wire as it enters and exits the spindle area. Additionally, a wire tension device is built into the mounting shaft. This tensioning device controls spool backlash that may occur during the unspooling process, and gives consistent delivery tension to the wire string.

A four-bank, four-plane static straightening method is used. This method of straightening tolerates the intermittent motion of a wire feed cycle. In one preferred arrangement, as it is unspooled, the wire is drawn through four banks of 11 rollers. As with the rotary setups, the inlet and outlet rollers (the first and the last) are for guiding purposes only. Each roller internal to the inlet and outlet rollers is adjusted until wire straightness is achieved. Each roller after this is adjusted in ever decreasing amounts of wire off-set, until the last roller is reached. This is called the wedge pattern. Once balance is attained, and enough offset is established for the rollers to work out the wire memory, a satisfactory setup is achieved.

Once the wire is straightened, the wire is cut into the desired length. The first step in actual needle making is to grind a sharp point on one end of the wire. While rotating the wire blank along its central longitudinal axis, it is presented to the grind wheel at a point on the surface of the cylindrical stone, perpendicular to the axis of rotation of the stone, to produce, for instance, a 45 degree angle on the point of the needle blank. This primary grinding is the first substantial grind that takes place in a typical taper point needle flow, where the needle takes on a shape very close to its final geometry. Here it is important to remove material accurately and efficiently, being careful not to heat the material to the point of annealing. The blanks are then transferred to another grinding machine, which grinds the desired point on the needles. Secondary grinding of tapered points is done to "finish" the surface and provide an optimum point. At least the last grinding wheel of this operation may be run opposite to the direction of rotation of the prior grinding, where the wheel is rotating towards the point. This produces a smaller burr and a sharper point.

Those skilled in the art of needlemaking are aware that grinding the needle point improves the needle performance when passing through tissue. A slender sharp point will have effective penetration performance through tissue. The spiral needle preferably has a taperpoint 12:1 geometry ground at the point; however, that ratio is not required. In fact, the needle could have a cutting edge, or tapercut point geometry if desired.

The spiral needle has a mechanically drilled hole at its barrel end for attaching a suture. The suture could also be attached to the needle using a laser drilled hole or a formed channel. All three methods are common practices for attaching a suture to a needle. To drill the hole in the barrel the needles are put onto a rotary machine that picks up the needles individually with chucks. The needle blank is first cut to the desired needle length with a press, which shears the wire. The next station drills a counter sink on the rear end of the needle with a high speed drill. After the countersink, another high speed drill mechanically drills a desired hole diameter and depth in the needle. The hole depth and diameter can vary depending upon the suture being attached.

The needles are then transferred to another rotary type machine which stamps the body of the needle. The desired flats and ribs are put on the needle body using a pneumatic press. Other acceptable ways of putting flats on the needle are hydraulic pressing and mechanical stamping. The ribs are designed to improve the handling of the needle in the needleholders. The spiral needle preferably has top and bottom flats with ribs; however, it could alternatively have a square, round or I-beam cross section.

Figure 2:
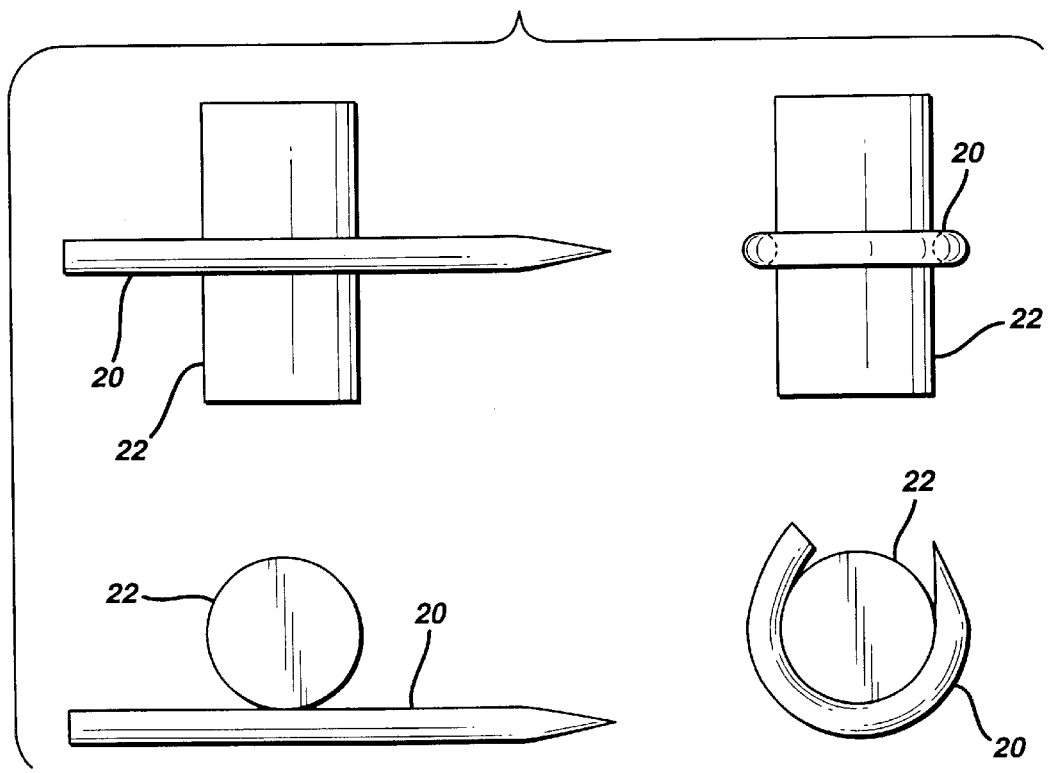
FIG. 2 is a schematic of a bending process for a conventional curved needle.

The curving and offsetting of the spiral needles are accomplished in a single operation on a rotary type machine. FIG. 2 shows a schematic of a conventional curving process, with side views at the top and top views below. At the left are shown needle 20 and curving mandrel 22 before the needle is curved. On the right are shown needle and mandrel after the needle has been curved around the mandrel.

Figure 3:
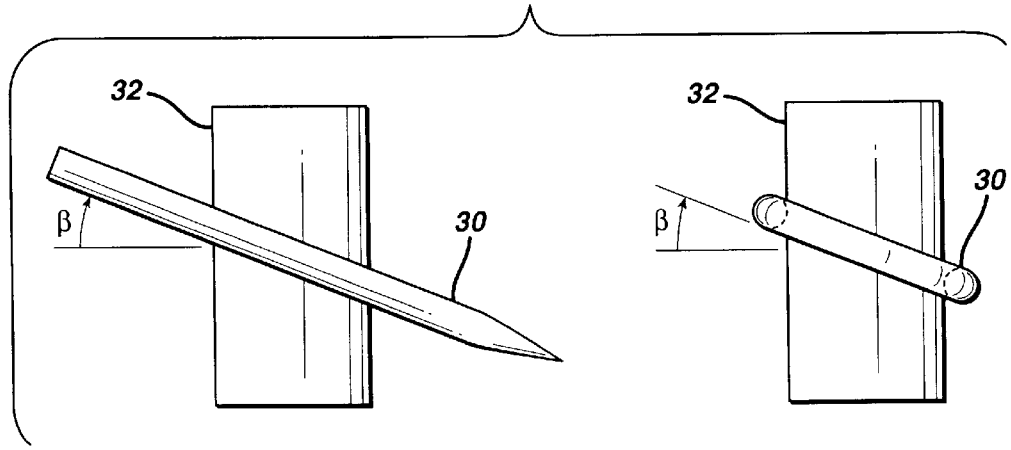
FIG. 3 is a schematic of a bending process for a needle of the present invention.

FIG. 3 depicts a side view of the spiral needle 30 of the present invention before (left) and after (right) bending around mandrel 32. The difference between the conventional needle bending process of FIG. 2 and the spiral needle bending process of FIG. 3 is that the conventional needle is positioned horizontally; i.e., normal to the cylindrical axis of the mandrel. The spiral needle is held at an angle β to the horizontal, preferably about ten degrees. Note that preferably, as shown in FIG. 3, curving mandrel 32 does not have a groove for the wire to follow.

In the manufacturing process (not shown), a manufacturing chuck is used to hand-off the needle blank to the feed mechanism. This chuck is mounted in a rotary arrangement. The stainless steel surgical needle is fed toward the curving mandrel on a line that is tangent to the mandrel's radius. The feed mechanism consists of a gripper that holds the needle at about a ten degree angle from the horizontal. After the needle is positioned and secured in the gripper, it is fed toward the mandrel by means of a pneumatic cylinder. The cylinder feeds the needle to a position that is tangent to the mandrel with the tangent point being approximately at the center of the needle blank. When the needle is in the desired position (tangent to the mandrel) a secondary pneumatic cylinder moves a holding pad, made from a suitable plastic, from a perpendicular direction. When the pad secures the needle, the gripper releases and returns to its initial position to allow for the next loading of a needle blank.

The mandrel for the spiral needle is designed to provide the spiral needle with more than 180 degrees of curvature. The preferred angle is approximately 243 degrees, however, angles greater or less than 243 are also suitable. If the needle is to have sections of different radius of curvature, the mandrel radius must differ along its circumference, accordingly. The mandrel also allows the needle to be formed in the shape of a helix because there are no grooves on the curving mandrel. The needle lateral offset is preferably between about 2 mm and 5 mm as a result of the mandrel shape and needle position prior to curving.

There are two mechanical rocker arms on each side of the holding pad cylinder, each connected to independent pneumatic cylinders, which drive the arms toward the needle mandrel. Each arm has rollers mounted in a position to facilitate the curving of the needle. The rollers can be manufactured from various materials, such as teflon, nylon, or kevlar. A blend of such materials, with other known plastics and fibers, are commercially available. The size of the rollers can vary, depending on the radius to be curved, and generally is from about 3 mm to 25 mm in diameter. The distance the roller travels around the mandrel can be adjusted to curve completely around the needle blank (full curve) or a lesser distance for a partial curve. As the rollers are driven toward the needle, and contact is made, the rocker arms pivot in order to allow the rollers the opportunity to follow the mandrel contour and curve the needle blank to the desired curvature. The rocker arms are spring loaded towards the mandrel, insuring the contour is followed. As a result of the needle position (preferably, about ten degrees from horizontal), the needle curvature will follow the desired mandrel but also provide a helical geometry to the curve.

After completion of the curving operation, the curved needle blank is dropped into a hopper or onto a conveyor for disposition. The needles are then heat treated. Heat treating surgical needles is well known in the field. The spiral needle is preferably 420 stainless steel. The needle is heat treated to provide the necessary strength and ductility for laparscopic procedures. The heat treatment process for 420 alloys involves multiple steps involving heating and quenching (cooling) and the temperature required is high. Basic equipment for the initial heat treatment process consists of a belt furnace, commercially available from Lindberg. Containers of needles are loaded on a mesh conveyor belt and transported through the oven, ultimately being heated to a range between 1800 and 1950° F., before being gas quenched to approximately 900° F. To prevent oxidation at higher temperatures, an atmosphere of nitrogen mixed with hydrogen is maintained inside the oven chamber. After completion of this phase of heat treatment, the needles are air cooled, and then placed in a convection oven (with or without an inert gas atmosphere) for tempering. Typical temperatures and times for this part of the cycle are from 400 to 500° F. for forty to sixty minutes.

The spiral needle is next electropolished in order to improve penetration and blackening characteristics. The needles are transferred to electropolishing for the elctrochemical removal of metal. This is an art that has been practiced in the industrial world for many years. Acid is used with electricity to react with metal to clean, deburr, and smooth the metallic surface. Approximately 0.005 mm to 0.01 mm of metal is removed during this process. The needles are washed in a batch after electropolishing.

After electropolishing and rinsing, the needles are blackened. The blackening is an oxidation of the polished needle surface to provide a dark, nonreflective surface that does not rub off, flake or peel. The blackening also does not degrade the sharpness of the needle. The blackened surface provides better visibility in a bloody field. Distilled water (750 ml), sodium dichromate (250 g) and sulfuric acid (250 ml) are mixed in a 2000 ml beaker. The solution is stirred using a magnetic stirrer until all the sodium dichromate has dissolved. The beaker is then placed in a hot water bath and heated to 65 degrees Celsius, after which the needles are placed into the beaker. The needles are removed from the beaker when they are sufficiently black. This process generally requires about twenty four hours. The needles are then rinsed in water for approximately one hour.

After the needles are rinsed, a batch quantity of needles are placed into a vacuum chamber containing sufficient distilled water to cover the needles. The water fills ("plugs") the holes, and the plugging process keeps the silicone coating process (described below) from filling the mechanically drilled hole. A low vacuum is held for about one minute.

Silicone is used on the spiral needle to act as a lubricant between the needle and the tissue. The performance of the needle piercing through tissue is improved when the needle is coated with the silicone. The spiral needle is coated using a triple dip process for the best penetration results. However, a single or double dip process can also be used. Silicone is extremely beneficial on a blackened needle.

A solution of silicone in an organic solvent (or solvents) is prepared, and the solution is stirred for about two hours. The silicone solution should not be used more than 48 hours after the time mixing is completed. Also the specific gravity of the solution should not exceed 0.702±0.003. The batch of needles is dipped into a silicone solution for approximately 15 seconds. Then the needles are removed and cured for more than one hour in an oven. This coating process is repeated three times.

The spiral needles are preferably attached to size 2/0 Ethibond Excel suture using a pneumatic pressing machine. Various other suture sizes and lengths may also be used with the spiral needle. Absorbable, non-absorbable, braided and monofilament sutures could all effectively be used with the spiral needle. The suture is placed into the drilled hole at the end of the needle. Then the pinching dies are pneumatically engaged. The walls of the needle are deformed until the suture is firmly attached. As stated earlier, the suture could be attached using a laser drilled hole or a formed channel as well. The crimping of the needle barrel to attach the suture can also be accomplished using a mechanical or hydraulic press.

We claim:

1. A needle for endoscopic surgery, comprising an elongated solid steel body formed into a generally arcuate shape, with a pointed distal end and a proximal end, in which:

(a) the needle is blackened
   (b) the needle is dimensioned to fit through a 10 mm diameter trocar; and (c) the body of the needle is not in a single plane, whereby there is a lateral offset of the distal end from the proximal end.

2. The needle of claim 1 in which the needle forms an arc of greater than 180°.

3. The needle of claim 2 in which the needle arc is greater than 225°.

4. The needle of claim 1 in which the body of the needle comprises a plurality of sections, each of which comprises an arc of a circle, having a predetermined radius.

5. The needle of claim 4 in which a central section of the needle comprises an arc of a first radius and each section that adjoins the central section comprises an arc of a second radius.

6. The needle of claim 4 in which the proximal section of the needle body is substantially linear.

7. The needle of claim 1 in which the lateral offset between the distal and proximal ends of the needle is in a range between about 2 mm and about 5 mm.

8. The needle of claim 7 in which the lateral offset is about 4 mm.

9. The needle of claim 1 in which the needle has a substantially circular cross section, having a diameter in the range from about 0.2 mm. to about 2 mm.

10. The needle of claim 9 in which the needle diameter is about 1 mm.

11. The needle of claim 9 in which the lateral offset is about four times the needle diameter.

* * * * *